United States Patent [19]

Stewart

[11] Patent Number: 5,197,498

[45] Date of Patent: Mar. 30, 1993

[54] DENTAL FLOSS HOLDING APPARATUS

[76] Inventor: Jeffrey A. Stewart, 1801 South Highland, Tacoma, Wash. 98465

[21] Appl. No.: 771,155

[22] Filed: Oct. 3, 1991

[51] Int. Cl.⁵ ............................................. A61C 15/00
[52] U.S. Cl. .................................... 132/325; 132/323; 132/326; 132/327
[58] Field of Search ............... 132/323, 325, 326, 327, 132/328, 329

[56] References Cited

U.S. PATENT DOCUMENTS

| | | | |
|---|---|---|---|
| 316,163 | 4/1991 | Brewer | D28/64 |
| 1,832,173 | 11/1931 | Yates | 132/323 |
| 2,187,442 | 1/1940 | Beach | 132/326 |
| 2,467,221 | 4/1949 | Pastl | 132/326 |
| 3,592,203 | 7/1971 | Johnson | 132/91 |
| 3,828,804 | 8/1974 | Ely | 132/91 |
| 3,903,907 | 9/1975 | Knaus | 132/92 R |
| 3,908,677 | 9/1975 | Beach | 132/91 |
| 3,910,294 | 10/1975 | Reed | 132/91 |
| 3,939,853 | 2/1976 | Spanondis | 132/91 |
| 3,960,159 | 6/1976 | Tesberg | 132/90 |
| 4,008,728 | 2/1977 | Sanchez | 132/92 R |
| 4,026,308 | 5/1977 | Krivit | 132/91 |
| 4,041,962 | 8/1977 | Johansson et al. | 132/91 |
| 4,051,857 | 10/1977 | Zamibito | 132/91 |
| 4,094,328 | 6/1978 | Ray | 132/325 |
| 4,192,330 | 3/1980 | Johnson | 132/91 |
| 4,194,290 | 3/1980 | Vallhonrat | 433/141 |
| 4,253,477 | 3/1981 | Eichman | 132/91 |
| 4,404,978 | 9/1983 | Withers | 132/91 |
| 4,508,125 | 4/1985 | Loubier | 132/92 R |
| 4,518,000 | 5/1985 | Leverette | 132/92 A |
| 4,556,074 | 12/1985 | Morin et al. | 132/92 R |
| 4,671,307 | 6/1987 | Curbow et al. | 132/91 |
| 4,706,694 | 11/1987 | Lambert | 132/92 R |
| 4,727,895 | 3/1988 | Berarducci | 132/91 |
| 4,736,757 | 4/1988 | Badoux | 132/323 |
| 4,738,271 | 4/1988 | Bianco | 132/92 R |
| 4,788,990 | 12/1988 | Wisegerber | 132/324 |
| 4,790,336 | 12/1988 | Kuo | 132/325 |
| 4,920,992 | 5/1990 | Preciutti | 132/323 |
| 4,920,993 | 5/1990 | Mackie | 132/324 |
| 4,982,752 | 1/1991 | Rodriguez | 132/327 |
| 5,016,660 | 5/1991 | Boggs | 132/322 |
| 5,038,806 | 8/1991 | Ewald | 132/325 |

Primary Examiner—Gene Mancene
Assistant Examiner—Cindy A. Cherichetti
Attorney, Agent, or Firm—Craine & Vance

[57] ABSTRACT

Apparatus and methods to hold and manipulate dental floss for the removal of plaque and food particles from teeth surfaces. The invention comprises: an elongated handle which may house, contain, and dispense a supply of dental floss; a stationary tong which does not generally move with respect to the handle; a pivotal tong which can be pivoted about a pivot point; means for securing the pivotal tong to the handle to selectively adjust the distance between terminal ends of the stationary tong and the pivotal tong; and means for anchoring the dental floss to the terminal ends of the stationary and pivotal tongs, the dental floss being positioned to span the distance and be pulled taut between the terminal ends of the tongs. Means for guiding the length of dental floss along the stationary and pivotal tongs and/or means for cutting the dental floss may also be provided.

35 Claims, 4 Drawing Sheets

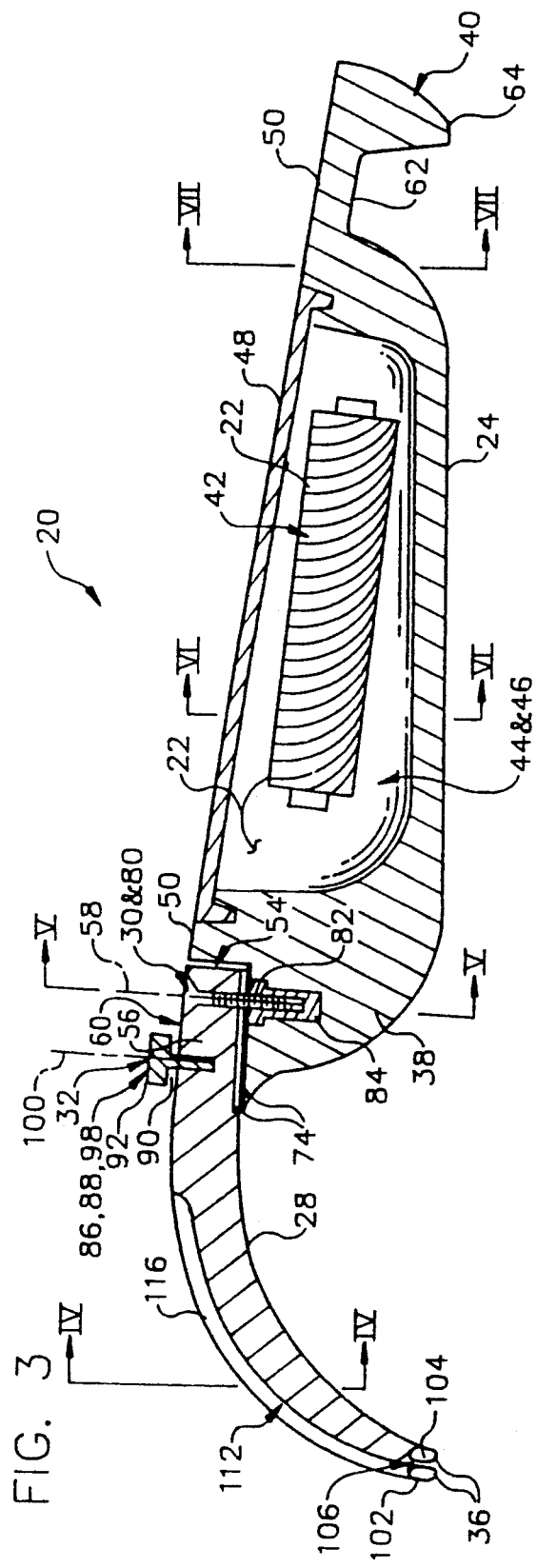
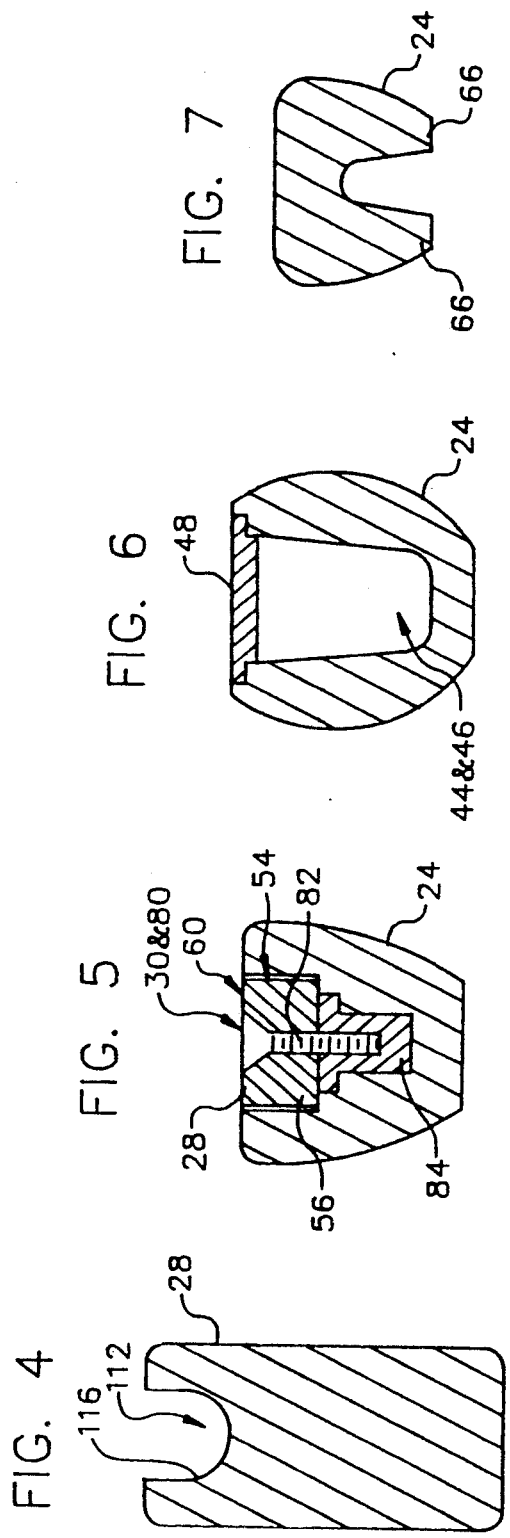

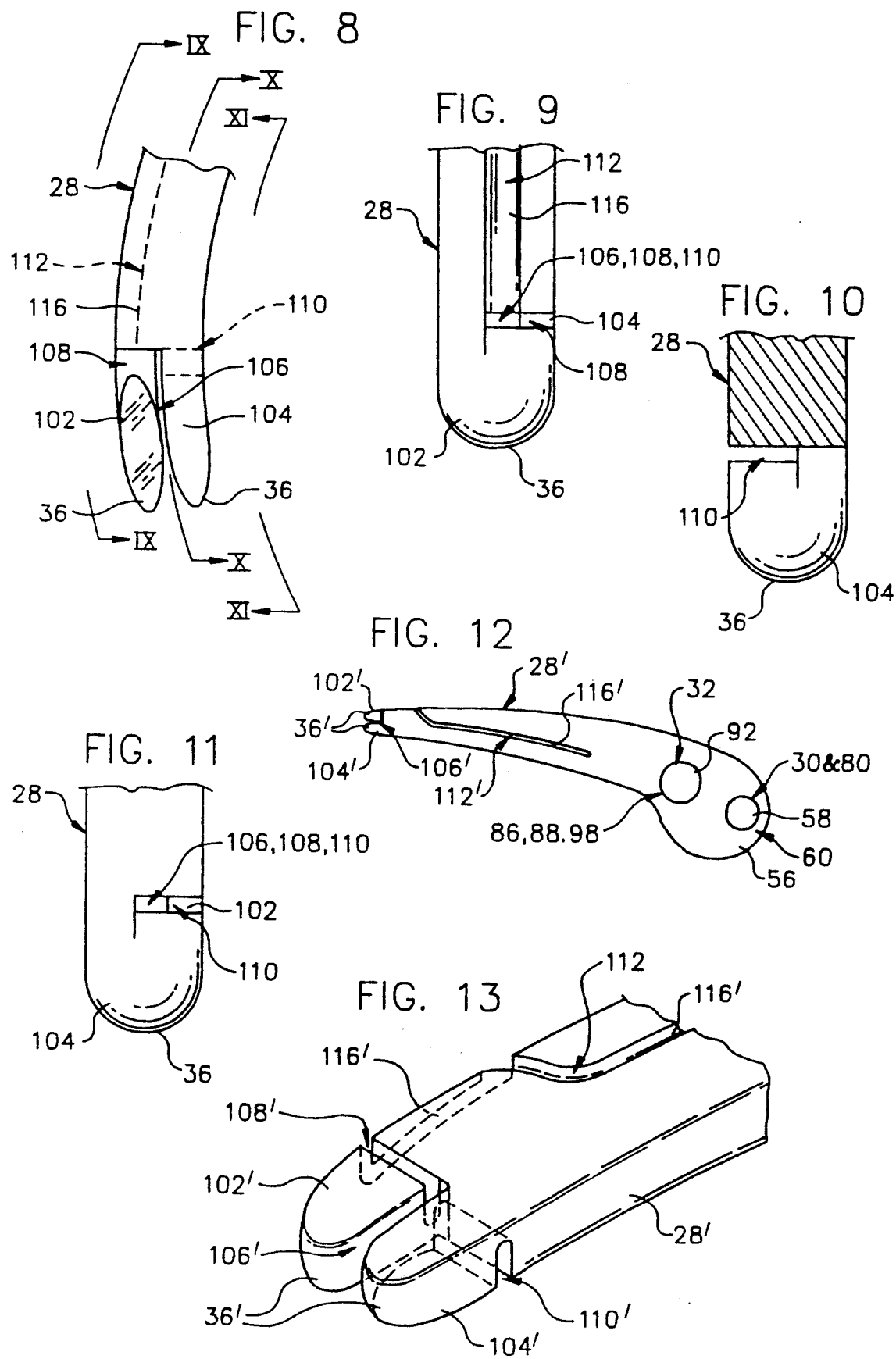

DENTAL FLOSS HOLDING APPARATUS

COPYRIGHT NOTICE

©Copyright 1991, Cassidy, Vance & Tarleton, P. S. All Rights Reserved.

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyrights whatsoever.

TECHNICAL FIELD

This invention relates to the technical field of oral hygiene devices used to remove plaque, microflora growth, and food particles from the surfaces of teeth to prevent the occurrence of dental caries and periodontal diseases. More particularly, this invention relates to apparatus and methods for storing, holding, dispensing, tensioning, and manipulating dental floss.

BACKGROUND OF THE INVENTION

Dental research has clearly identified that the primary causative agents of dental caries and periodontal diseases are the build-up of plaque and growth of oral microflora on the coronal and root surfaces of teeth. Plaque build-up is accelerated by the presence of solid food particles and dissolved food constituents which tend to adhere to teeth surfaces. It is also well established that proper oral hygiene, consisting of regularly scouring plaque from the surfaces of teeth, reduces the occurrence of dental caries and periodontal diseases. Oral hygiene is most effective when it is practiced immediately after eating.

The toothbrush is a widely used implement to scour or clean teeth. Even though brushing with a toothbrush is an effective way to clean dental surfaces which oppose the cheeks, lips and tongue, it is less effective to scour or clean plaque from the interproximal surfaces or interstitial areas of teeth. The interproximal surfaces of teeth are those tooth surfaces which face and often contact other tooth surfaces.

Another popular oral hygiene tool is the toothpick. A toothpick is generally a thin sliver of wood or plastic with tapered ends. One end of the toothpick is urged between the teeth to force out larger food particles which may have become entrapped therebetween.

A variety of dental instruments known as scalers and probes are also commonly used by dentists and oral hygienists. A scaler has a probe end with a cutting surface used to remove tartar from teeth. A dental probe has a pointed end which is usually bent from the longitudinal axis of the handle and is used to locate indentations and cavities in teeth. Many configurations are known but such instruments are designed for use by health professionals and are not suited, or intended, for general public use.

Dental floss is the most commonly used implement to scour or clean the interproximal surfaces of teeth. Dental floss is a strong, thin thread. The respective ends of the dental floss are wound about the index finger on each hand of the user. The free length of floss located between the user's fingers is pulled back and forth through the spaces between the teeth. As the thread is pulled, the surfaces of the thread are urged onto the interproximal surfaces of the teeth, thereby scouring and removing food and plaque from those areas of the teeth.

This method of applying dental floss is very wasteful since the terminal ends of the floss are not used and are discarded. In addition, many people have a great deal of difficulty mastering the techniques of correctly using and administering hand-held dental floss. The manipulation of the floss requires a high order of dexterity. The fingers of the user must be inserted into the mouth which can be unsanitary, cumbersome, uncomfortable, and distasteful. The user's fingers become coated with saliva and it is difficult to maintain a solid grip on the floss. The working area within one's mouth is limited which increases the difficulty in using this method of oral hygiene.

Consequently, many different devices have been created to assist in the manipulation and use of dental floss. The following issued patents describe various devices for holding dental floss: Tesberg (U.S. Pat. No. 3,960,159; issued Jun. 1, 1976); Krivit (U.S. Pat. No. 4,026,308; issued May 31, 1977); Johansson et al. (U.S. Pat. No. 4,041,962; issued Aug. 16, 1977); Johnson (U.S. Pat. No. 4,192,330; issued Mar. 11, 1980); Withers (U.S. Pat. No. 4,404,978; issued Sep. 20, 1983); Morin et al. (U.S. Pat. No. 4,556,074; issued Dec. 3, 1985); Lambert (U.S. Pat. No. 4,706,694; issued Nov. 17, 1987); Bianco (U.S. Pat. No. 4,738,271; issued Apr. 19, 1988); Wisegerber (U.S. Pat. No. 4,788,990; issued Dec. 6, 1988); and Kuo (U.S. Pat. No. 4,790,336; issued Dec. 13, 1988).

The inventor believes that the listed patents taken alone or in combination neither anticipate nor render obvious the present invention. These citations do not constitute an admission that such disclosures are relevant or material to the present claims. Rather, these citations relate only to the general field of the disclosure and are cited as constituting the closest art of which the inventor is aware.

DISCLOSURE OF INVENTION

Dental research has clearly identified that the removal of food particles and plaque from teeth greatly reduces the occurrence of dental caries and periodontal diseases. This invention is an improved interproximal oral hygienic tool for the removal of such food particles and plaque from teeth. Its design was generated from a consideration for the anatomy of the dentition and age of the user, including the structural relationship between the jaw, teeth, bone and the soft interdental gingiva, and for its ease of utilization.

This invention may be used not only to dislodge food particles, but also to abrade and scour plaque formations from teeth and stimulate adjacent gum tissue. These benefits are coupled with an advantageous design which enables the tool to be easily used with a simultaneous facial and palatal/lingual approach to reach the interproximal surfaces of both the maxillary and mandibular teeth. The invention is simple, functional, efficient, reliable, rugged, durable, compact, and is easily used, constructed, and assembled.

To accomplish the foregoing and other objectives, the invention generally comprises: (a) a handle; (b) a stationary tong; (c) a pivotal tong; (d) means to pivotally or fixedly secure the pivotal tong to the handle; and (e) means to removably anchor a length of dental floss to the terminal ends of both the stationary and pivotal tongs.

The handle is configured and is of such a size to allow easy holding and manipulation. The handle may also comprise an enclosure to contain, shield, and dispense a supply of dental floss.

The stationary tong and pivotal tong extend divergently outward from a fore end of the handle. The ability of the apparatus to scour plaque from the surfaces of the teeth is enhanced because of the invention's ability to adjust the distance between the terminal ends of the stationary and pivotal tongs. This feature allows the invention to be adjusted for the various sizes and shapes of palates and mandibular anatomy. The invention may be adjusted to fit the mouth opening and teeth of the user. For example, the invention may be easily adjusted to fit a child's mouth and teeth. The invention may also be adjusted to provide shorter or longer lengths of dental floss which are capable of having a wide variety of tension forces. If the tension within the dental floss is increased, deeper penetration of the floss into the interproximal areas and increased surface contact with the teeth is achieved. Increased tension within the dental floss also enables the floss to pass more easily between contact points located between adjacent teeth.

Adjustment of the distance between the pivotal and stationary tongs is accomplished by means of selectively securing the pivotal tong in either a pivotal or fixed position with respect to the handle. When released, the pivotal tong may rotate to any one of numerous angular positions with respect to the handle and stationary tong. When fixedly secured, the pivotal tong may be used to effectively support a length of dental floss in a stretched taut state between the terminal ends of the stationary and pivotal tongs.

The invention is provided with any one or a combination of a wide variety of means for anchoring each end of the dental floss to the terminal ends of the stationary and pivotal tongs to maintain a stretched taut state.

Unfortunately, dental floss has a tendency to break. Frequently, a single strand of dental floss will only work between a single pair of teeth. This means that during one complete usage of up to 28 spaces, an individual user may be required to load and unload a dental floss holder/dispenser twenty-eight (28) different times. It was not uncommon in the prior art that the user was required to thread a terminal end of the dental floss through an extremely small aperture or hole after each time the dental floss broke.

In stark contrast to the prior art, the preferred embodiment of the present invention uses a much more efficient and effective means for anchoring the dental floss to the terminal ends of the stationary and/or pivotal tongs. More particularly, such anchoring means comprises two or more interacting cleats positioned on the terminal ends of the stationary and/or pivotal tongs. These cleats and the other elements of the present invention are described in greater detail below.

Other features such as means for guiding a length of the dental floss along the stationary and pivotal tongs, and means for cutting off excess lengths of dental floss may also be provided.

The present invention achieves each of the above-stated objectives and also overcomes the previously mentioned disadvantages of the prior art.

These and other objectives and advantages of the present invention will become more readily apparent upon reading the following disclosure and referring to the attached drawings.

BRIEF DESCRIPTION OF DRAWINGS

FIG. 3 is a cross-sectional, side-elevational view of the first embodiment taken through path III—III of FIG. 1, which is along the length of the handle and pivotal tong.

FIG. 4 is a cross-sectional, side-elevational view taken through line IV—IV of FIG. 3.

FIG. 5 is a cross-sectional, side-elevational view taken through line V—V of FIG. 3.

FIG. 6 is a cross-sectional, side-elevational view taken through line VI—VI of FIG. 3.

FIG. 7 is a cross-sectional, side-elevational view taken through line VII—VII of FIG. 3.

FIG. 8 is an enlarged, partial, side-elevational view of the terminal end of the pivotal tong shown in FIG. 2.

FIG. 9 is an enlarged, partial, plan view of the terminal end of the pivotal tong taken through line IX—IX of FIG. 8.

FIG. 10 is an enlarged, partial, cross-sectional, bottom plan view of the terminal end of the pivotal tong taken through line X—X of FIG. 8.

FIG. 11 is an enlarged, partial, plan view of the terminal end of the pivotal tong taken through line XI—XI of FIG. 8.

FIG. 12 is an alternative, second embodiment of the pivotal tong which may be used with the handle illustrated in FIG. 1.

FIG. 13 is an enlarged, partial, isometric view of the terminal end of the pivotal tong illustrated in FIG. 12.

Figure 1:
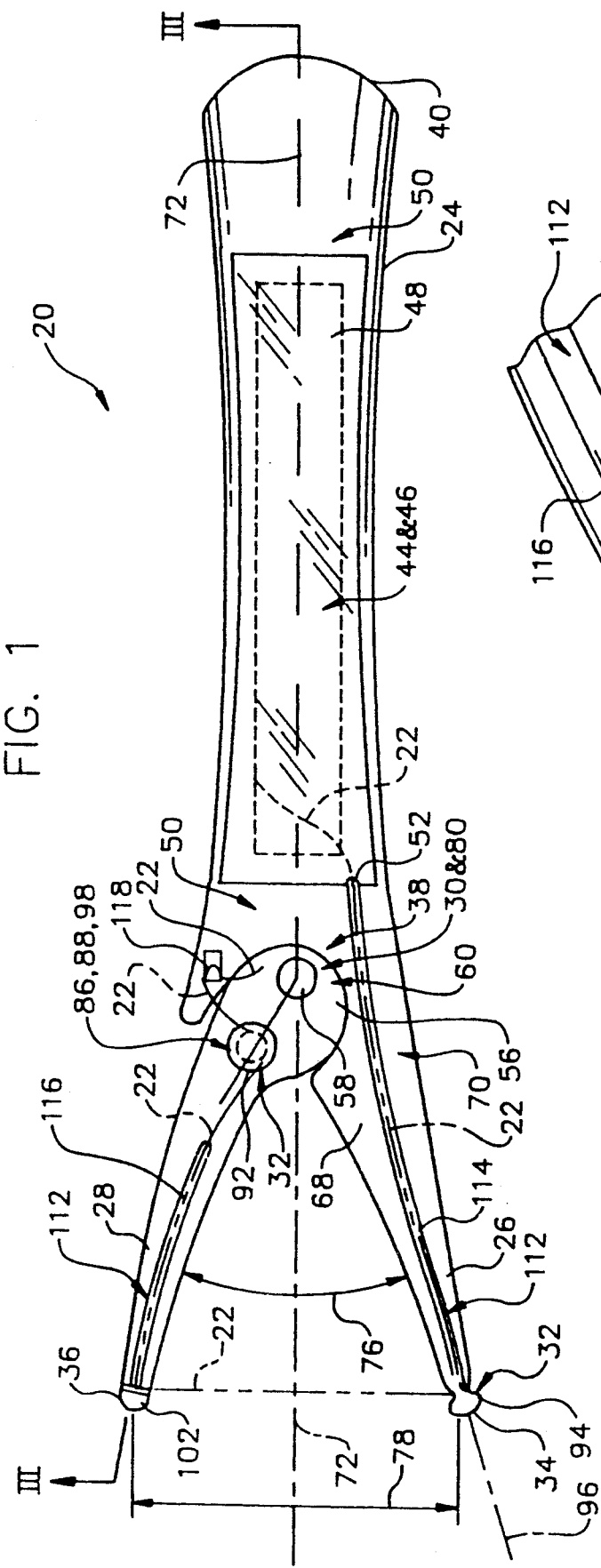
FIG. 1 is a plan view depicting the general appearance of the first embodiment of the invention.
Figure 2:
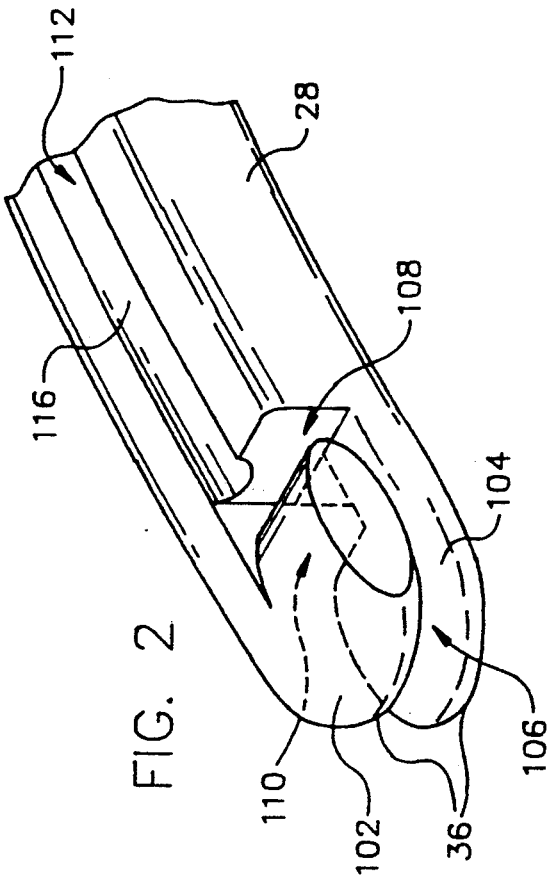
FIG. 2 is an enlarged, partial, isometric view of the terminal end of the pivotal tong illustrated in FIG. 1.
Figure 14:
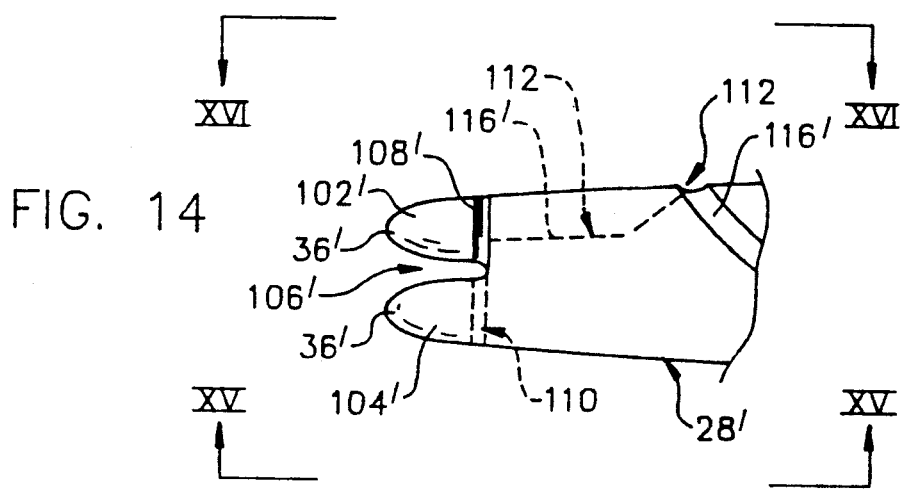
FIG. 14 is an enlarged, partial, plan view of the terminal end of the pivotal tong shown in FIG. 12 taken through line XIV—XIV in FIGS. 15 and 16.
Figure 15:
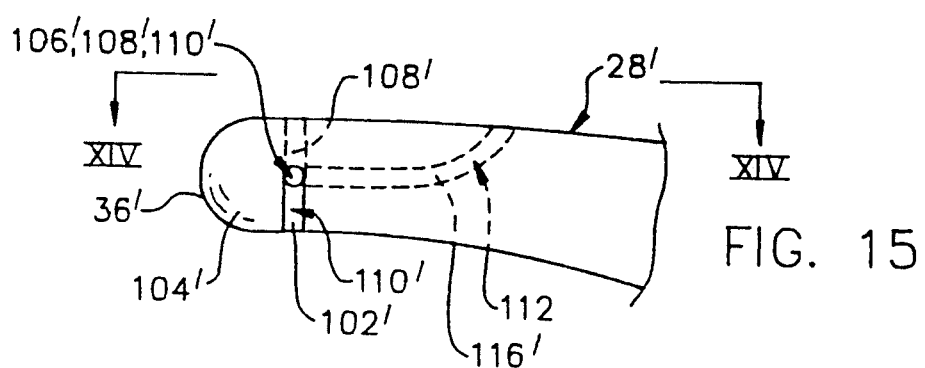
FIG. 15 is an enlarged, partial, side-elevational view of the terminal end of the pivotal tong taken through line XV—XV of FIG. 14.
Figure 16:
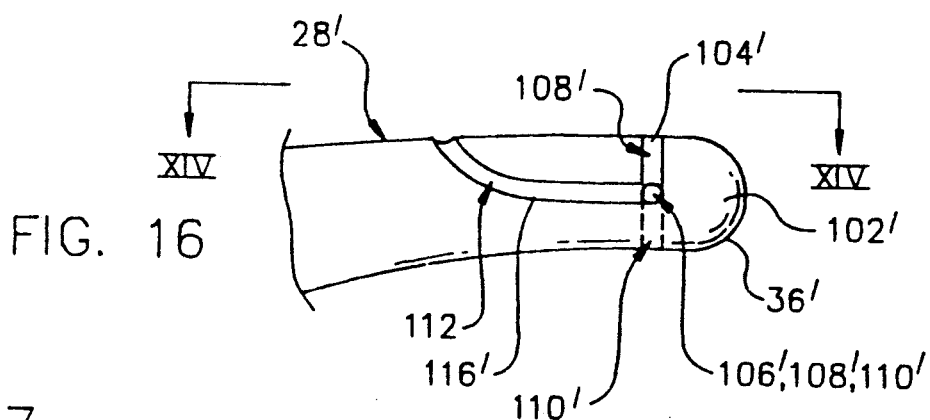
FIG. 16 is an enlarged, partial, side-elevational view of the terminal end of the pivotal tong taken through line XVI—XVI of FIG. 14.

One should understand that the drawings are not necessarily to scale and the elements are sometimes illustrated by graphic symbols, phantom lines, diagrammatic representations, and fragmentary views. In certain instances, the inventor may have omitted details which are not necessary for an understanding of the present invention or which render other details difficult to perceive.

BEST MODE FOR CARRYING OUT THE INVENTION

Referring to the drawings, wherein like numerals indicate like parts, an apparatus 20 of the present invention may be used to manipulate a length of dental floss 22 stretched under tension to abrade and remove plaque and food particles from interproximal surfaces of teeth (not shown). Apparatus 20 generally comprises: (a) a handle 24; (b) a stationary tong 26; (c) a pivotal tong 28; (d) means 30 to pivotally or fixedly secure pivotal tong 28 to handle 24; and (e) means 32 to removably anchor dental floss 22 to terminal ends 34 and 36 of stationary and pivotal tongs 26 and 28, respectively.

HANDLE

Handle 24 of apparatus 20 is designed and adapted to be easily grasped, held, and manipulated by one hand of a user. The design of handle 24 imparts a mechanical advantage to apparatus 20 to scour plaque from teeth surfaces. To accomplish these ends, handle 24 comprises an elongated structure having a fore end 38 and an aft end 40.

Preferably, handle 24 has an irregular configuration to permit ease of digital utilization and manipulation, and for portability. For example, as best seen in FIG. 1, handle 24 may have a generally concavo-concave configuration when viewed from above. FIGS. 5, 6 and 7 illustrate various cross sections of handle 24 as seen along corresponding lines of FIG. 1. It should be clear, however, that handle 24 may take any configuration or cross-sectional shape which accomplishes the desired objectives. Any regular or irregular shaped handle 24, having ridges, indentations or a textured surface, would similarly provide means to manipulate apparatus 20.

Handle 24 may also be adapted to hold and dispense a supply 42 of dental floss 22. If desired, handle 24 defines the boundaries of an enclosure 44, receptacle, or reservoir within which supply 42 is housed, contained, and dispensed. For example, as shown in FIG. 3, handle 24 may be formed with an elongated downwardly extending well 46 which defines enclosure 44. Well 46 of handle 24 provides convenient and efficient means to manipulate apparatus 20.

Handle 24 may also be provided with an irregular outer surface which is slightly roughened or textured to assist in digital manipulation. Similarly, any irregular surface could be used, including ridges running laterally or longitudinally along portions of the outer surface of handle 24.

Apparatus 20 may also be provided with a lid 48 which is removably secured to handle 24. Removal of lid 48 permits access to the interior of enclosure 44. As best shown in FIGS. 1 and 3, lid 48 may serve as an upper surface 50 for handle 24. Lid 48 is provided with an orifice 52, hole, or opening which allows one end of the supply 42 of dental floss 22 to extend outwardly from enclosure 44. Orifice 52 is shown in FIG. 1.

As best seen in FIGS. 1 and 3, handle 24 is provided with a recess 54 configured to receive a pivotal end 56 of pivotal tong 28. Recess 54 has sufficient depth and size to allow pivotal end 56 of pivotal tong 28 to rotate about a pivot point 58. Pivot point 58 will be discussed at length further below.

In the preferred embodiment, upper surface 60 of pivotal tong 28 and upper surface 50 of handle 24 are generally coplanar when pivotal end 56 is positioned within recess 54.

As best seen in FIGS. 3 and 7, aft end 40 of handle 24 generally has a thinner portion 62 which extends rearwardly from well 46 or enclosure 44. Aft end 40 may further have at least one downwardly extending portion 64 which extends downwardly from thinner portion 62. As seen in FIG. 7, downwardly extending portion 64 may have a pair of opposed, spaced-apart structures or wings 66 which extend downwardly therefrom.

STATIONARY TONG

Stationary tong 26 is an elongated member having a fixed end 68 and outwardly-projecting terminal end 34. Fixed end 68 is contiguous with handle 24. This may be accomplished by either integrally forming fixed end 68 to fore end 38, or by fixedly securing fixed end 68 thereto so that stationary tong 26 generally maintains a fixed orientation with respect to handle 24. In the preferred embodiment, upper surface 70 of stationary tong 26 is generally coplanar with upper surface 50 of handle 24 at their union and intersection.

Both stationary tong 26 and pivotal tong 28 extend divergently outward from fore end 38 of handle 24.

The size, shape, and length of stationary tong 26 and pivotal tong 28 are primarily dependent upon the size of the user's mouth and teeth, and the access area and manual dexterity available to the user. Preferably, the shape of stationary tong 26 and pivotal tong 28 is designed to allow deep penetration of dental floss 22 between teeth and allow greater contact with interproximal surfaces as compared to a conventional toothbrush or toothpick. For example, stationary and pivotal tongs 26 and 28 may be bent arcuately downward from fore end 38 of the handle 24 to give the tongs a general appearance of a claw or nike. The general configuration of the side of pivotal tong 28 can be best seen in FIG. 3. Stationary tong 26 has a similar bent configuration. This shape allows the user to easily reach over the mandibular teeth and engage the interproximal areas between the maxillary teeth.

As seen in FIG. 1, stationary tong 26 may also be bent arcuately inward toward the position of pivotal tong 28. Similarly, pivotal tong 28 may be bent arcuately inward toward the position of stationary tong 26.

Stationary and pivotal tongs 26 and 28 should be slender enough to permit their insertion and manipulation within the mouth of the user.

Terminal ends 3 and 36 contain the working tips of the invention which hold and stretch the length of dental floss 22 therebetween. It is these terminal ends 34 and 36 and the length of dental floss 22 which are inserted into the mouth of the user. Consequently, the respective terminal ends 34 and 36 of stationary and pivotal tongs 26 and 28 should each have a generally rounded, blunt apex or tip to prevent puncturing or injuring the user's interdental gingiva. Terminal ends 34 and 36, however, are designed to accommodate retention of dental floss 22 while still urging dental floss 22 against the interproximal surface contours of the teeth.

Terminal ends 34 and 36 are preferably formed from a continuation of stationary tong 26 and pivotal tong 28 or are integrally attached thereto. Terminal ends 34 and 36 may be molded integrally with the material forming stationary and pivotal tongs 26 and 28 to avoid the hazard of having an attached end or tip detach during use.

Apparatus 20 should also be fabricated from a material soft enough to avoid damage to teeth but hard enough to adequately support and manipulate the taut dental floss 22 to readily scour plaque from teeth surfaces.

Apparatus 20 is also made of a material which is non-toxic, strong, flexible, resilient, reusable, and can be manufactured quickly and inexpensively. For example, handle 24 and stationary tong 26 can be integrally molded from a material such as CELCON plastic. CELCON is a trademark for a highly crystalline acetal copolymer based on trioxane and is described also as a polyoxymethylene thermal plastic polymer obtained by ionically initiated copolymerization of formaldehyde to obtain a linear molecule. CELCON plastic has the properties of being hard, rigid, strong, resilient, and dimensionally stable under exposure to moisture and heat. This material is available from the DuPont de Nemours, E. I. and Company. A different material could also be used if it would achieve the desired objectives.

In the preferred embodiment, stationary and pivotal tongs 26 and 28 are made of a material having sufficient flexibility that, when dental floss 22 is stretched taut therebetween and is urged against the interproximal surfaces of teeth, stationary and pivotal tongs 26 and 28 may deflect slightly.

PIVOTAL TONG

Pivotal tong 28 is also an elongated, outwardly-projecting member which is contiguous with handle 24. Pivotal tong 28 has pivotal end 56 and an outwardly-projecting terminal end 36. When attached to handle 24, pivotal end 56 may be selectively secured in either a pivotal or fixed position. Thus configured, pivotal tong 28 may be pivoted and then secured within a wide angular range of motion with respect to elongated handle 24. For example, pivotal tong 28 may move anywhere between a position of about ten (10) degrees left of a center line 72 of handle 24, which is generally toward or parallel to stationary tong 26, and a position of about forty (40) degrees right of center line 72, diverging away from stationary tong 26.

Pivotal end 56 and fore end 38 may also each be provided with raised ridges 74, spines, spikes, or protuberances, and/or with recessed areas, such as channels or indentations, which extend radially outward from pivot point 58. Raised ridges 74 on pivotal end 56 and fore end 38 are positioned and juxtaposed to interlock one another between pivotal tong 28 and handle 24. Interlocking raised ridges 74 assist pivotal tong 28 to assume one of a plurality of angular orientations or positions with respect to handle 24 and stationary tong 26. In the preferred embodiment, interlocking raised ridges 74 permit pivotal tong 28 to be selectively secured in any one of up to twenty (20) different angular orientations with respect to handle 24 and stationary tong 26.

SECURING MEANS

Securing means 30 generally defines pivot point 58 about which pivotal tong 28 may rotate. Securing means 30 also enables pivotal end 56 to be selectively, pivotally or fixedly secured to handle 24. In other words, securing means 30 permits the selective adjustment of a generally acute angle 76 between stationary tong 26 and pivotal tong 28, and permits selective adjustment of a distance 78 between terminal ends 34 and 36.

Thus, securing means 30 may be used to adjust acute angle 76 and distance 78 and then secure pivotal tong 28 to handle 24 to generally maintain a fixed orientation with respect to handle 24 and with respect to stationary tong 26.

As generally shown in FIGS. 3 and 5, securing means 30 may comprise a threaded compression bolt 80 or screw which in turn defines pivot point 58. A bore hole 82 is located in pivotal end 56 of pivotal tong 28. Compression bolt 80 passes through bore hole 82 to engage fore end 38 of handle 24. When tightened, compression bolt 80 forces pivotal end 56 into tight engagement with fore end 38 of handle 24. Friction between pivotal end 56 and handle 24 holds pivotal tong 28 in place.

As specifically seen in FIGS. 3 and 5, securing means 30 may further include an insert 84 having internal threads. Insert 84 is secured to fore end 38 of handle 24 and is positioned about pivot point 58. The outer threads of compression bolt 80 are capable of interlocking with the interior threads of insert 84. Thus configured, compression bolt 80 and insert 84 may be tightened and compressed together to fixedly secure pivotal tong 28 in fixed orientation with respect to handle 24.

ANCHOR MEANS

The invention also comprises anchoring means 32 to removably anchor dental floss 22 near or against terminal ends 34 and/or 36 of stationary and pivotal tongs 26 and 28. When secured, securing means 30 and anchoring means 32 permit the length of dental floss 22 to be stretched taut and span across distance 78 between the respective terminal ends 34 and 36 of the stationary and pivotal tongs 26 and 28.

An extremely simple anchoring means 32 may comprise at least one anchoring or fastening device 86 secured to either handle 24, to stationary tong 26, and/or to pivotal tong 28. It would be preferable to have fastening device 86 positioned near either: the fore end 38 of handle 24; the fixed end 68 of stationary tong 26; the pivotal end 56 of pivotal tong 28; or at any other convenient location on apparatus 20.

One end of dental floss 22 is wrapped or otherwise secured to fastening device 86. A central portion of dental floss 22 is passed along stationary tong 26 to terminal end 34, is stretched across distance 78 toward terminal end 36, and is then passed back to be secured to fastening device 86.

Fastening device 86 may comprise a generally cylindrical raised boss 88, knob, or capstan extending substantially perpendicular from either handle 24, stationary tong 26, or pivotal tong 28. Dental floss 22 is wrapped around boss 88 to securely yet removably hold and retain dental floss 22 thereto. Boss 88 necessarily has a contracted inner portion 90 or slot and an enlarged, outwardly-extending, outer portion 92. Inner portion 90 is configured to capture and removably retain the length of dental floss 22.

In the preferred and more complex embodiment of the invention, anchoring means 32 may further comprise at least one supply capstan 94 or boss located near terminal end 34 of stationary tong 26. Supply capstan 94 basically serves as a cleat to securely yet removably hold and retain dental floss 22 to terminal end 34. One end of the length of dental floss 22 may be wrapped around supply capstan 94 and be secured thereto.

Figure 17:
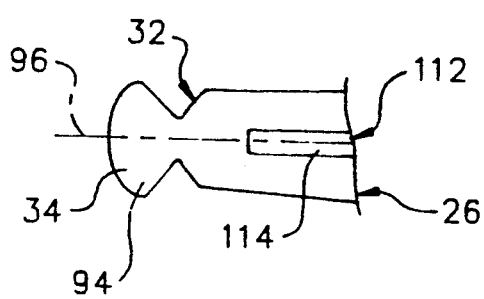
FIG. 17 is an enlarged, partial, plan view of the terminal end of the stationary tong shown in FIG. 1.

As shown in FIGS. 1 and 17, supply capstan 94 may have an axis 96 which is generally coaxial with an axis of terminal end 34 of stationary tong 26.

As best seen in FIGS. 1 and 3, anchoring means 32 may further comprise at least one takeup capstan 98 which is secured to handle 24. Takeup capstan 98 enables the remaining end of the length of dental floss 22 to be wrapped and secured thereto. Thus, the length of dental floss 22 passes from supply capstan 94, is stretched taut between terminal ends 34 and 36 of stationary tong 26 and pivotal tong 28, and is then secured to takeup capstan 98. Takeup capstan 98 may have an axis 100 which is generally transverse or perpendicular to an adjacent upper surface 50 of handle 24.

The contour of terminal ends 34 and 36 is determined primarily by the size and type of dental floss 22 to be held. Thus, the shape of terminal ends 34 and 36 dictates the ease of attaching and anchoring dental floss 22 thereto, and the degree of resistance dental floss 22 has to becoming detached therefrom.

Reference is now made to two different embodiments of anchoring means 32 which may be located at terminal end 36 of pivotal tong 28. The first embodiment is illustrated in FIGS. 1, 2, 3, 8, 9, 10, and 11. An alternative, second embodiment is illustrated in FIGS. 12, 13, 14, 15, and 16.

Generally speaking, anchoring means 32 may further comprise at least two interacting cleats 102 and 104 which are positioned at terminal end 34 and/or at terminal end 36. In the preferred embodiments, cleats 102 and 104 are positioned at terminal end 36 of pivotal tong 28. Cleats 102 and 104 have a generally thin slit 106 therebetween which enables the length of dental floss 22 to pass therebetween. Cleat 102 has a slot 108 and cleat 104 has a slot 110 positioned generally transversely to slit 106. Slots 108 and 110 permit the length of dental floss 22 to be turned transversely within slit 106. Thus inserted, cleats 102 and 104 allow the easy insertion and attachment of dental floss 22 to terminal end 36 of pivotal tong 28. Insertion of dental floss 22 into slit 106 and slots 108 and 110 is simple and easy even for users having low dexterity. Cleats 102 and 104 prevent removal of the dental floss 22 through slit 106 when dental floss 22 is positioned and stretched taut within slots 108 and 110. Cleats 102 and 104 also prevent removal of the dental floss 22 through slit 106 when dental floss 22 is slack. For example, dental floss 22 is first secured to terminal end 34 and is then pulled tight to anchor 86. No threading of terminal end 36 is necessary or required. Dental floss 22, however, still remains securely retained in its position. This feature gives the present invention a major advantage over devices heretofore invented.

Cleats 102 and 104 in the first embodiment are positioned with a generally horizontal orientation, such that cleat 102 is directed toward stationary tong 26 and cleat 104 is directed away from stationary tong 26.

Pivotal tong 28' of the second embodiment is provided with corresponding reference numerals as shown on pivotal tong 28 of the first embodiment, except where a distinction is necessary and then an apostrophe (') is included with the reference numeral. Therefore, terminal end 36' of pivotal tong 28' of the second embodiment is similarly provided with cleats 102' and 104'. Cleats 102' and 104' are positioned with a generally vertical orientation, such that cleat 102' is directed upward and cleat 104' is directed downward. Similar to cleats 102 and 104 of the first embodiment, cleats 102' and 104' of the second embodiment have slit 106' and slots 108' and 110'.

The tips or terminal ends 34 and 36 of stationary and pivotal tongs 26 and 28 should be generally rounded and have a blunt end to prevent the tips from puncturing or injuring the interdental gingiva of the user. If cleats 102 and 104, or 102' and 104', and supply capstan 94 are used, they likewise are configured with generally rounded and blunt ends.

GUIDING MEANS

Although not required, the present invention may also comprise means 112 for guiding the length of dental floss 22 from anchoring means 32 toward respective terminal ends 34 and 36 of stationary tong 26 and pivotal tong 28.

As illustrated in FIGS. 1 and 17, guiding means 112 may comprise a groove or elongated first channel 114 formed at least along a portion of stationary tong 26. First channel 114 receives, protects, and guides at least a portion of the length of dental floss 22 which may be laid therein and positioned along stationary tong 26 between anchoring means 32 and terminal end 34.

FIGS. 1, 2, 3, 4, 8, and 9 illustrate the first embodiment of the invention wherein guiding means 112 also comprises a groove or elongated second channel 116 formed at least along a portion of pivotal tong 28. Second channel 116 receives, contains, protects, and guides at least a portion of the length of dental floss 22 which may be laid therein and positioned along the length of pivotal tong 28 between anchoring means 32 and terminal end 36. Second channel 116 generally extends linearly along a longitudinal length of pivotal tong 28.

Similarly, FIGS. 12, 13, 14, 15, and 16 illustrate the second embodiment of the invention wherein guiding means 112 comprises a differently configured groove or elongated second channel 116' formed at least along a portion of pivotal tong 28. In the second embodiment, first channel 114' and second channel 116' further wrap around from a top to one side of pivotal tong 28 and from stationary tong 26.

If supply capstan 94 is not used on terminal end 34, then guiding means 112 may further comprise one or more slits and/or slots (not shown) formed near or at terminal ends 34 and 36. Such slits and/or slots receive and retain a portion of the dental floss 22 to prevent slippage of the dental floss 22 from terminal ends 34 and 36 when the floss 22 is stretched taut and used.

CUTTING MEANS

The present invention may also further comprise means 118 for cutting the length of dental floss 22. For example, as shown in FIG. 1, cutting means 118 of a conventional configuration may be secured to handle 24. Alternatively, cutting means 118 may be secured to stationary tong 26 and/or to pivotal tong 28.

Many different versions of this invention may be made by varying the configuration and contour of handle 24, stationary tong 26, and/or pivotal tong 28. Similarly, this invention could be made with two pivotal tongs 28, rather than with one pivotal tong 28 and one stationary tong 26 as described above. There are also a wide variety of other types of securing means and anchoring means, such as clamps, pins, etc., that could be alternatively used to accomplish the same objectives as set forth herein.

The means and construction disclosed herein are by way of example and comprise primarily the preferred form of putting the invention into effect. Although the drawings depict a preferred embodiment of the invention, other embodiments have been described within the preceding text. One skilled in the art will appreciate that the disclosed device may have a wide variety of shapes and configurations. Additionally, persons skilled in the art to which the invention pertains might consider the foregoing teachings in making various modifications, other embodiments, and alternative forms of the invention.

It is, therefore, to be understood that the invention is not limited to the particular embodiment or specific features shown herein. To the contrary, the inventor claims the invention in all of its forms, including all modifications, equivalents, and alternative embodiments which fall within the legitimate and valid scope of the appended claims, appropriately interpreted under the Doctrine of Equivalents.

INDUSTRIAL APPLICABILITY

The industrial applicability of this invention can be readily ascertained by reference to the following example of its use.

During use, the distance between the stationary and pivotal tongs is initially adjusted to properly accommodate the size of the user's teeth. This is accomplished by releasing means to secure the pivotal tong to the handle. Once the pivotal tong is able to pivot, it is positioned with the correct or desired distance between the terminal ends, and the securing means is retightened to securely affix the pivotal tong to the handle.

A terminal end of a length of dental floss is grasped by the user's other hand and a sufficient length of approximately five to eight inches (5"-8") of dental floss is pulled from a reservoir within the handle. The dental floss should be of a sufficient thickness to permit insertion between the teeth and to approximate the contour thereof. The length of dental floss is directed into guiding means located along the length of the stationary tong and is then securely wrapped around the terminal end of the stationary tong.

The tips or terminal ends of the stationary and pivotal tongs are generally rounded and have a blunt end to prevent the tips from puncturing or injuring the interdental gingiva.

The remaining terminal length of dental floss is stretched taut across the distance between the terminal ends of the stationary and pivotal tongs.

The dental floss is inserted into a slit in the terminal end of the pivotal tong and is then turned transversely to the direction of the slit. This structure causes the dental floss to engage respective slots in at least two interacting cleats formed at the terminal end of the pivotal tong.

The dental floss is pulled taut and is directed into guiding means located along the length of the pivotal tong. The terminal end of the dental floss is then securely wrapped around securing means positioned either on the pivotal tong or on the handle.

The remaining terminal end of the dental floss may then be pulled across cutting means to sever off any excess length of dental floss.

Once the pivotal tong and dental floss are secured, the user manipulates the handle to carefully insert the terminal ends or working tips of the stationary tong and pivotal tong into the mouth. The tongs are positioned on opposite sides of the teeth, one tong on the facial side and the other tong on the palatal/lingual side of the teeth, such that the length of dental floss is inserted into the interproximal spaces between the maxillary or mandibular teeth.

The handle is then manipulated so that the dental floss contacts and abrades against the interproximal surfaces of the teeth. The dental floss gives the apparatus a mechanical advantage to abrade and scour plaque from teeth. Movement of the apparatus and attached dental floss dislodges food particles from between the teeth and scours and removes plaque and microflora growth from the surfaces of the teeth. The user continues manipulating the apparatus going from anterior to posterior teeth on both dental arches.

For example, the angled terminal end of the stationary tong may be used to hold the dental floss near the anterior and posterior interproximal surfaces of the dentition of both arches from the facial direction. The angled terminal end of the pivotal tong is used to hold the dental floss near the anterior and posterior interproximal surfaces of both dental arches from the palatal/lingual direction.

The process to replace the portion of floss being used is extremely simple. The user simply detaches the floss from the pivotal tong, bypassing the tip of the pivotal tong. The user detaches the floss from the stationary tong cleat by unwrapping it and pulls out a few inches of new floss from the reservoir. The new segment of floss is then secured to the stationary tong cleat, and is pulled tight across to the pivotal tong cleats. The terminal end of the floss is then secured. Once the floss is initially strung within the pivotal tong tip, the floss will not become tangled or require any serious attention of the user, until the floss breaks which requires the floss to be restrung. The foregoing process simply requires wrapping and unwrapping of the floss from the cleats at the ends of the stationary tong and the pivotal tong. Consequently, very little waste of floss occurs and the requirement dexterity on the part of the user is minimal.

I claim:

1. An apparatus adapted to be held by a hand of a user for holding and manipulating a length of dental floss under tension to abrade and remove plaque and food particles from interproximal surfaces of teeth, comprising:

(a) an elongated handle configured for hand manipulation, said handle having a fore end and an aft end;

(b) an elongated, outwardly-projecting stationary tong contiguous with said handle, said stationary tong having a fixed end and an outwardly-projecting terminal end, said fixed end being formed integrally with or fixedly secured to said handle, said stationary tong generally maintaining a fixed orientation with respect to said handle;

(c) an elongated, outwardly-projecting pivotal tong contiguous with said handle, said pivotal tong having a pivotal end and an outwardly-projecting terminal end, said pivotal end being selectively pivotally or fixedly secured to said handle;

(d) means for selectively pivotally or fixedly securing said pivotal end to said handle, said securing means defining a pivot point about which said pivotal tong may rotate, said stationary tong and said pivotal tong generally extending divergently from said fore end of said handle, said securing means permitting selective adjustment of a generally acute angle between said stationary tong and said pivotal tong, said securing means permitting selective adjustment of a distance between said terminal ends of said stationary tong and pivotal tong, said securing means permitting said pivotal tong to be fixedly secured to said handle to generally maintain a fixed orientation with respect to said handle and with respect to said stationary tong; and means for removably anchoring the length of dental floss near or against said terminal ends of said stationary tong and said pivotal tong, said securing means and said anchoring means permitting the length of dental floss to be stretched taught and span a distance between said terminal ends of said stationary tong and said pivotal tong, said pivotal end of said pivotal tong and said fore end of said handle being each provided with raised ridges radially extending from said pivot point, said raised ridges being positioned and juxtaposed to interlock one another between said handle and said pivotal tong, said interlocking raised ridges assisting said pivotal tong to assume one of a plurality of angular orientations or positions with respect to said handle and said stationary tong.

2. The apparatus of claim 1, wherein a central portion of said handle is narrower in width than respective ends of said handle.

3. The apparatus of claim 1, wherein said handle is adapted to hold and dispense a supply of dental floss, said handle defining an enclosure, receptacle, or reservoir within which a supply of dental floss may be housed, contained, and dispensed.

4. The apparatus of claim 3, wherein said handle is formed with an elongated downwardly extending well which defines said enclosure.

5. The apparatus of claim 3, further comprising a lid removably secured to said handle, removal of said lid permitting access to said enclosure.

6. The apparatus of claim 5, wherein said lid forms an upper surface of said handle.

7. The apparatus of claim 1, wherein said handle has a recess configured to receive said pivotal end and allow said pivotal tong to rotate about said pivot point, said pivotal tong and said handle having generally coplanar upper surfaces when said pivotal end is positioned within said recess.

8. The apparatus of claim 1, wherein said aft end of said handle comprises a generally thinner portion extending rearwardly from said aft end and at least one downwardly extending portion extending from said thinner portion.

9. The apparatus of claim 8, wherein said downwardly extending portion comprises a pair of opposed, spaced-apart structures or wings.

10. The apparatus of claim 1, wherein said stationary tong and said pivotal tong are generally coplanar, each being arcuately bent downward from said fore end of said handle.

11. The apparatus of claim 1, wherein said terminal ends of said stationary tong and said pivotal tong each have a generally blunt apex or tip.

12. The apparatus of claim 1, wherein said stationary tong and said pivotal tong have sufficient flexibility that when the dental floss is stretched taut and is urged against the interproximal surfaces of teeth, said stationary tong and said pivotal tong deflect slightly to allow the length of dental floss to assume a curvature which generally conforms to the interproximal surfaces of the teeth.

13. The apparatus of claim 1, wherein said securing means comprises a threaded compression screw or bolt, said compression screw or bolt passing through a bore hole located in said pivotal end of said pivotal tong to engage said fore end of said handle, said compression screw or bolt defining said pivot point.

14. The apparatus of claim 13, wherein said securing means further comprises an insert having internal threads, said insert being secured to said fore end of said handle and positioned about said pivot point, said insert and said compression screw or bolt being capable of interlocking to fixedly secure said pivotal tong in fixed orientation with respect to said handle.

15. The apparatus of claim 1, wherein said interlocking raised ridges permit said pivotal tong to be selectively secured in any one of up to twenty different said angular orientations with respect to said handle and said stationary tong.

16. The apparatus of claim 1, wherein said pivotal tong has a range of motion with respect to said elongated handle of between about 10 degrees left of a center line of said handle, which is generally toward or parallel to said stationary tong, and about 40 degrees right of said center line diverging away from said stationary tong.

17. The apparatus of claim 1, wherein said anchoring means comprises at least one fastening device secured to said handle, to said stationary tong, or to said pivotal tong for holding opposite end portions of the dental floss.

18. The apparatus of claim 17, wherein said fastening device comprises a generally cylindrical boss extending substantially perpendicular from said handle, from said stationary tong, or from said pivotal tong, said boss defining a raised cleat or knob around which the dental floss may be wrapped to securely yet removably hold and retain the dental floss, said boss having a contracted inner portion or slot and an enlarged outer portion, said inner portion being configured for capturing and removably retaining the length of dental floss.

19. The apparatus of claim 17, wherein said fastening device is positioned near said fore end of said handle.

20. The apparatus of claim 17, wherein said fastening device is positioned near said fixed end of said stationary tong.

21. The apparatus of claim 17, wherein said fastening device is positioned near said pivotal end of said pivotal tong.

22. The apparatus of claim 17, further comprising means for guiding the length of dental floss from said anchoring means toward said terminal ends of said stationary tong and said pivotal tong.

23. The apparatus of claim 22, wherein said guiding means comprises a groove or elongated first channel formed at least along a portion of said stationary tong, said first channel receiving, protecting, and guiding the length of dental floss along said stationary tong between said anchoring means and said terminal end of said stationary tong.

24. The apparatus of claim 22, wherein said guiding means comprises a groove or elongated second channel formed at least along a portion of said pivotal tong, said second channel receiving, containing, protecting, and guiding the length of dental floss which may be laid therein along said pivotal tong between said anchoring means and said terminal end of said pivotal tong, said second channel generally extending linearly along a longitudinal length of said pivotal tong.

25. The apparatus of claim 24, wherein said second channel of said guiding means further wraps around form a top to one side of said pivotal tong.

26. The apparatus of claim 1, wherein said anchoring means further comprises at least one supply capstan secured to said stationary tong and positioned near said terminal end, the length of dental floss being wrapped around said supply capstan and secured thereto, said supply capstan serving as a cleat to securely yet removably hold and retain the dental floss.

27. The apparatus of claim 26, wherein said supply capstan has an axis which is generally coaxial with an axis of said terminal end of said stationary tong.

28. The apparatus of claim 26, wherein said anchoring means further comprises at least one takeup capstan secured to said handle, said takeup capstan enabling the length of dental floss to be wrapped and secured thereto.

29. The apparatus of claim 28, wherein said takeup capstan has an axis which is generally transverse or perpendicular to an adjacent surface of said handle.

30. The apparatus of claim 1, wherein the length of dental floss passes from said supply capstan, is stretched taut between said terminal ends of said stationary tong and said pivotal tong, and is secured to said takeup capstan.

31. The apparatus of claim 1, further comprising means for cutting the length of dental floss.

32. The apparatus of claim 31, wherein said cutting means is secured to said handle.

33. The apparatus of claim 31, wherein said cutting means is secured to said stationary tong.

34. The apparatus of claim 31, wherein said cutting means is secured to said pivotal tong.

35. The apparatus of claim 1, wherein said guiding means comprises one or more slots formed near or at said terminal ends of said stationary and said pivotal tongs, said slots receiving and retaining a portion of the dental floss to prevent slippage of the dental floss from said terminal ends of said stationary and said pivotal tongs when the floss is pulled taught.

* * * * *

UNITED STATES PATENT AND TRADEMARK OFFICE
CERTIFICATE OF CORRECTION

PATENT NO. : 5,197,498
DATED : March 30, 1993
INVENTOR(S) : Jeffrey A. Stewart

It is certified that error appears in the above-identified patent and that said Letters Patent is hereby corrected as shown below:

Column 6, line 33, delete "3" and insert therefor --34--.

Column 12, line 56, insert --(e)-- immediately preceding "means".

Column 12, line 60, delete "taught" and insert therefor --taut--.

Column 14, line 51, delete "form" and insert therefor --from--.

Column 16, line 22, delete "taught" and insert therefor --taut--.

Signed and Sealed this

Twenty-fifth Day of January, 1994

Attest:

BRUCE LEHMAN

Attesting Officer    Commissioner of Patents and Trademarks